United States Patent
Petkov et al.

(10) Patent No.: US 10,665,007 B2
(45) Date of Patent: May 26, 2020

(54) HYBRID INTERACTIVE MODE FOR RENDERING MEDICAL IMAGES WITH RAY TRACING

(71) Applicant: Siemens Healthcare GmbH, Erlangen (DE)

(72) Inventors: Kaloian Petkov, Lawrenceville, NJ (US); Daphne Yu, Yardley, PA (US)

(73) Assignee: Siemens Healthcare GmbH, Erlangen (DE)

( * ) Notice: Subject to any disclaimer, the term of this patent is extended or adjusted under 35 U.S.C. 154(b) by 33 days.

(21) Appl. No.: 15/871,418

(22) Filed: Jan. 15, 2018

(65) Prior Publication Data

US 2019/0221027 A1 Jul. 18, 2019

(51) Int. Cl.
| | |
|---|---|
| *G06T 15/06* | (2011.01) |
| *G06T 15/08* | (2011.01) |
| *G06T 13/80* | (2011.01) |
| *G06T 15/50* | (2011.01) |
| *A61B 5/00* | (2006.01) |
| *G06T 7/00* | (2017.01) |
| *G06T 15/20* | (2011.01) |

(52) U.S. Cl.
CPC ............ *G06T 15/06* (2013.01); *A61B 5/0035* (2013.01); *G06T 7/0012* (2013.01); *G06T 13/80* (2013.01); *G06T 15/08* (2013.01); *G06T 15/503* (2013.01); *A61B 5/0066* (2013.01); *G06T 15/205* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 9,401,044 B1* | 7/2016 | Kaufman | G06T 17/10 |
| 9,947,136 B2* | 4/2018 | Serlie | G06T 15/00 |
| 2006/0274065 A1* | 12/2006 | Buyanovskiy | G06T 15/06 |
| | | | 345/424 |
| 2007/0211055 A1 | 9/2007 | Stein et al. | |
| 2008/0024493 A1* | 1/2008 | Bordoloi | G06T 15/08 |
| | | | 345/423 |
| 2010/0149213 A1* | 6/2010 | Navab | G02B 27/017 |
| | | | 345/633 |

(Continued)

FOREIGN PATENT DOCUMENTS

WO 2017039664 A1 3/2017

OTHER PUBLICATIONS

Kroes et al ("Interactive direct volume rendering with physically-based lighting", Eurographics, 2012) (Year: 2012).*

(Continued)

*Primary Examiner* — Xin Sheng

(57) ABSTRACT

For interactive rendering in medical imaging, physically-based volume rendering of a volume of a patient may better assist physicians in diagnosis, prognosis, and/or planning. To provide for more rapid interaction, direct volume rendering is used during interaction. The rendering then transitions to physically-based rendering when there is no interaction. For smoothing the transition and/or preserving cohesive perceptual details, images from the different types of rendering may be blended in the transition and/or during interaction.

20 Claims, 3 Drawing Sheets
(1 of 3 Drawing Sheet(s) Filed in Color)

(56) References Cited

U.S. PATENT DOCUMENTS

| | | | |
|---|---|---|---|
| 2014/0029849 A1* | 1/2014 | Sen | G06T 15/503 |
| | | | 382/167 |
| 2015/0062100 A1* | 3/2015 | Tanaka | G09G 3/3648 |
| | | | 345/204 |
| 2016/0350963 A1 | 12/2016 | Petkov et al. | |
| 2017/0061687 A1 | 3/2017 | Hong et al. | |
| 2017/0308656 A1 | 10/2017 | Petkov et al. | |
| 2017/0352181 A1 | 12/2017 | Vetter et al. | |

OTHER PUBLICATIONS

Novák, Jan, Vlastimil Havran, and Carsten Dachsbacher. "Path regeneration for interactive path tracing." Eurographics (Short Papers). 2010.

Extended European Search Report (EESR) dated Apr. 15, 2019 in corresponding European Patent Application No. 19151409.0.

Petkov, Kaloian et al; "Frameless Volume Visualization"; IEEE Transactions on visualization and computer graphics; IEEE Service center, Los Alamitos ; vol. 22; No. 2; pp. 1076-1087.

Ammann, Lucas et al; "Hybrid rendering of dynamic heightfields using ray-casting and mesh rasterization"; Proceedings; Canadian information processing society; pp. 161-168.

Hauswiesner, Stefan et al; "Multi-Frame Rate Volume Rendering"; Eurographics / IEEE VGTC Symposium on Volume Graphics (8th IEEE/EG International Symposium on Volume Graphics; Volume Graphics 2010; Co-located with the Annual Conference of the European Association for Computer Graphics; Eurographics 2010; pp. 1-8.

* cited by examiner

HYBRID INTERACTIVE MODE FOR RENDERING MEDICAL IMAGES WITH RAY TRACING

BACKGROUND

The present embodiments relate to rendering in medical imaging. For three-dimensional visualization, different rendering approaches may be used. In traditional volume rendering (e.g., direct volume rendering), each pixel of the final image is sampled along the viewing direction (i.e., rays) as a direct function of collected samples within the viewing volume. Each image sample on the viewing direction of one pixel is classified as a color sample and then composited to the final image. Direct volume rendering may be performed rapidly.

Another approach is physically-based rendering. A type of physically-based volume rendering is the Monte Carlo path tracing, which is a useful rendering technique for light transport computations, where the natural light phenomena are modeled using a stochastic process. Physically-based rendering may produce a number of global illumination effects not provided by direct volume rendering. Such effects include ambient light occlusion, soft shadows, color bleeding, and depth of field, all of which increase the realism of the produced images and improve user performance on perceptually-based tasks. Since evaluation of the rendering integral may require thousands of stochastic samples per pixel to produce an acceptably noise-free image, physically-based rendering uses more processing and is slower than direct volume rendering. Depending on the rendering parameters, rendering an image may take on the order of seconds for interactive workflows and multiple hours for production-quality images. Making alterations to the rendering in interactive workflows may be time consuming with physically-based volume rendering. In medical imaging, this use of time leads to increased costs.

SUMMARY

By way of introduction, the preferred embodiments described below include methods, systems, instructions, and computer readable media for interactive rendering in medical imaging. Physically-based volume rendering of a volume of a patient may better assist physicians in diagnosis, prognosis, and/or planning. To provide for more rapid interaction, direct volume rendering is used during interaction. The rendering then transitions to physically-based rendering when there is no interaction. For smoothing the transition and/or preserving cohesive perceptual details, images from the different types of rendering may be blended in the transition and/or during interaction.

In a first aspect, a method is provided for interactive rendering in medical imaging. A medical scanner scans a volume of a patient. The scanning acquires intensities representing the volume. During interaction by a user, a sequence of first two-dimensional images are rendered to a display from the intensities with direct volume rendering. Upon the interaction ceasing for a period, a second two-dimensional image is rendered to a display from the intensities with path tracing rendering.

In a second aspect, a system is provided for interactive rendering in medical imaging. A medical imaging system is configured to scan an internal region of a patient and generate voxel data representing a volume comprising the internal region. A user interface is configured to receive user input of one or more changes to rendering parameters. A renderer is configured to render first images of the volume from the voxel data with raycasting using the rendering parameters. The first images are rendered with the raycasting during a period within a threshold time of the receipt of any of the one or more changes. The renderer is also configured to render second images of the volume from the voxel data with physically-based rendering at times outside of the period. The times outside of the period occur where user input of the one or more changes does not occur. A display is configured to display the first images and the second images as a sequence where the first and second images representing the internal region.

In a third aspect, a method is provided for interactive rendering in medical imaging. Physically-based volume rendering of an internal region of a patient is performed. A real-time frame rate is maintained during user interaction to change the physically-based volume rendering with raycasting. A sequence of images, including images from the physically-based volume rendering and the raycasting, are displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A hybrid interactive mode for physically-based volume rendering allows for rapid rendering during interaction. A computationally simplified technique, as compared to the full path tracing pipeline of physically-based rendering, is used for evaluating the rendering integral during interaction. The rendering during interaction may be rapid through the use of caching approaches as well to improve the interactive performance. The interactive image is blended with the progressively updating final image from path tracing using different heuristics, such as based on the interactive rendering algorithm and various image-based metrics. A selftuning step may be implemented to more closely match the interactive and final image features.

The hybrid approach addresses the challenge of providing a highly interactive workflow when using a physically-based volume renderer that produces photorealistic images at a significantly larger computational cost compared to the traditional raycasting volume renderer. The interactive framerate (e.g., 20 frames per second or more) is particularly desirable for common medical visualization tasks, such as changing of transfer function classification to reveal different parts of the anatomy in the three-dimensional (3D) images, 3D camera rotation, clipping away structures, and/or lighting manipulation. A change in one or more of these controls may defeat the internal caching in the renderer and trigger expensive re-computation during interaction, lowering the framerate and often reducing the image to an impractical image quality. Providing the direct volume rendering during interaction instead provides a representative visualization that preserves important features from the final image, while allowing accurate parameter editing at interactive framerates.

Figure 1:
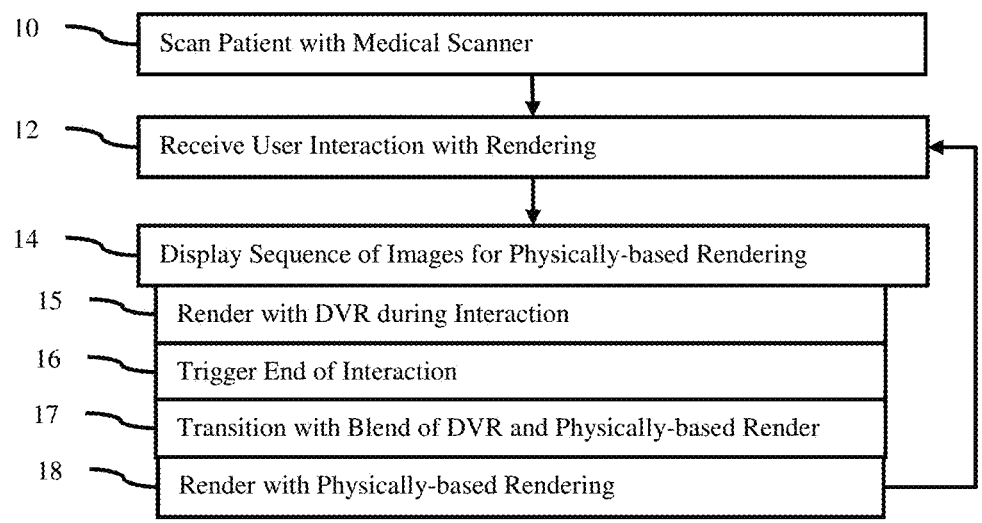
FIG. 1 is a flow chart diagram of one embodiment of a method for rendering in medical imaging.

FIG. 1 shows a method for interactive rendering in medical imaging. Physically-based rendering, such as ray tracing, is used to render images from a scan volume. The physically-based volume rendering provides an image of an internal region of the patient. Where the viewer desires to alter the image, the viewer interacts with the rendering. To provide for more rapid interaction or responsiveness to change, direct volume rendering, such as raycasting, is used to more rapidly render images during the interaction. Once the change is complete, the rendering transitions back to the more detailed or desired physically-based volume rendering.

Figure 5:
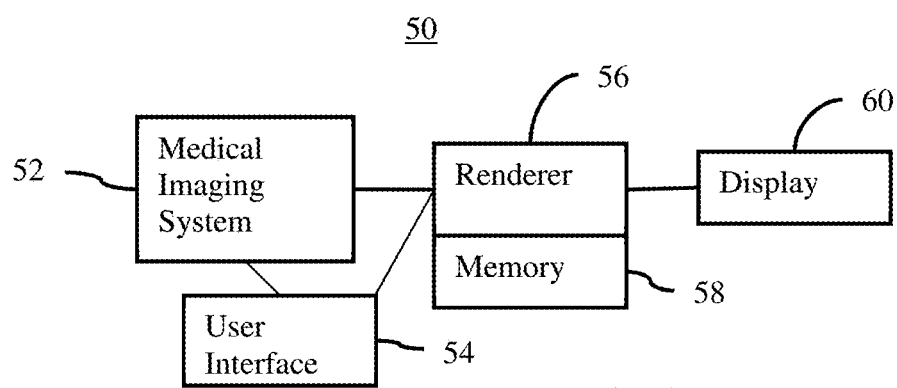
FIG. 5 is a block diagram of one embodiment of a system for rendering in medical imaging.

The method is implemented by the system 50 of FIG. 5 or another system. For example, act 10 is performed by a medical scanner, act 12 is performed by a user input or interface, and acts 14-18 are performed by a renderer and a display device. Any one or more of the acts may be performed by different devices.

The acts are performed in the order shown or other orders. For example, direct volume rendering (DVR) of act 15 and physically-based rendering of act 18 may be combined as part of rendering in act 15 for interaction and/or rendering in act 17 during the transition. Act 18 may be performed before act 12, such as generating an image for initial user interaction.

Additional, different, or fewer acts may be provided. For example, an initial image is rendered after act 10 and before act 12. As another example, act 10 is not performed. Instead, the scan data is loaded from a memory or received over a computer network. In another example, act 17 is not performed, but instead the rendering directly changes from DVR to physically-based rendering.

The method is performed using a static volume. Based on a given scan, the voxels are used to render a sequence of images. As the user interacts, the same voxels or intensities are used for rendering subsequent images to eventually create a viewer desired image. The images are generated from the same scan data or volume. In other embodiments, the method is repeated in real-time with an on-going acquisition in medical imaging, such as imaging moving anatomy. Repetition may be provided for interactive rendering and/or representing an object moving in the patient.

In act 10, a medical scanner acquires a set of voxels. The set represents a volume of the patient. A volume of a patient is scanned with the medical scanner. The interior of the patient is scanned, such as with magnetic resonance (MR), x-ray (e.g., CT), ultrasound, or emission tomography (e.g., PET or SPECT). The scan is performed in any format, such as detecting emissions along lines of response, acquiring k-space data at magnetic gradient defined locations, or acquiring projections through the patient with x-rays from different directions.

A renderer or the medical imaging system reconstructs a volume representing, at least in part, the internal portion of the patient. Any reconstruction from the scan data may be used. Tomography or other process may be used to determine intensities for different locations distributed in three dimensions. As a result of the scan, data representing the interior of the patient in an N×M×O region or volume is acquired, where N, M, and O are integers greater than 1. The reconstruction determines scalar values or intensities for each of a plurality of voxels distributed in three dimensions.

In alternative embodiments, the intensities are classified as color. For example, a classification or transform function is applied to convert the intensities to red, green, blue, opacity (RGBa) values or color values. The color values are used instead of intensities.

The intensities represent response from blood, tissue, bone, other object, and/or contrast agents in the patient. In one embodiment, the voxel data is computed tomography data representing bones with or without tissue of the patient. In another embodiment, the voxel data is magnetic resonance data representing tissue of the patient.

After scanning, the render generates an initial image from the voxel data. The renderer renders an image from the intensities representing the volume of the patient. The three-dimensional distribution of voxels or intensities is rendered to a two-dimensional image for display. The pixel values of the two-dimensional image are determined from the voxel values of the three-dimensional distribution. The pixels values may then be used on the two-dimensional screen or display. The image is rendered to the display, but may be rendered and provided to a memory or network.

The rendering uses path or ray tracing, implementing physically-based rendering. Raycasting projects rays through a volume and examines the intensities along each ray to create a pixel value for the image. For example, the maximum intensity along each ray is found and used. As another example, the intensities along the ray are combined in a weighted average, where the weight is based on opacity or magnitude of the intensity. Conversely, ray or path tracing is used in physically-based rendering. Rays are projected from each pixel. Light is simulated along each of the rays. The scattering, absorption, and/or emission of the light may be simulated with stochastic interaction. Many photons or light samples are simulated for each ray. The color or intensity resulting from the scattering, absorption, and/or emission along each ray is calculated.

In Monte Carlo-based physical rendering, contribution from the volume samples to the final image are based on simulation of interactions between light projected from the viewpoint to the volume structure along the ray paths. The probabilities are solved for along each of a plurality of rays traced from pixels with Monte Carlo ray tracing. To create the image with physically-based rendering, the full rendering equitation is evaluated so that the result approximates the real-world interaction between light and matter. In comparison, direct volume rendering methods often account for the direct illumination only, or a subset of the global illumination effects (e.g., only forward-scattering of light, or only ambient occlusion in addition to direct illumination). In Monte Carlo path tracing, Monte Carlo numerical methods are used to solve the integral over all light paths in the rendering equation. In practical terms, dozens to thousands of light paths are constructed between the observer's viewpoint (e.g., through pixels on the imaging plane/viewport) and light sources in the scenes, accounting for light scattering from surfaces in the scene. The surfaces may be defined by the medical images, computer assisted design (CAD) models of medical devices, implicit or explicit surfaces, measurements, clip planes, or other techniques.

Figure 2:
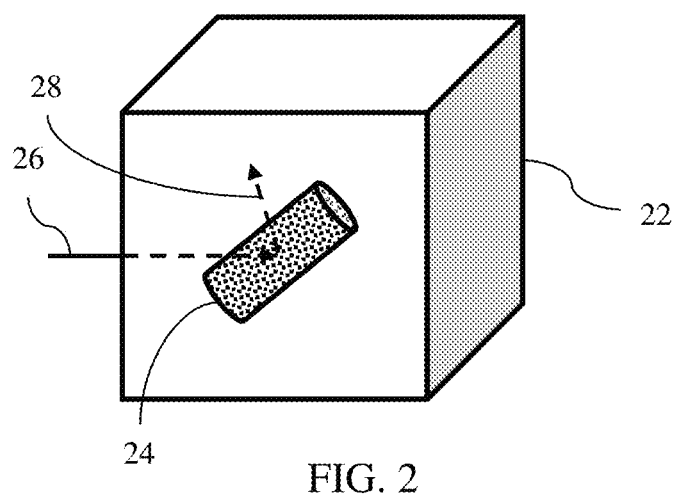
FIG. 2 illustrates an example embodiment of a volume and a ray.

FIG. 2 shows an example. A ray 26 is traced from a pixel or view into the volume 22. The ray 26 intersects tissue. For a given photon or light sample, the light may pass through some tissue, but the Monte Carlo simulation indicates a scattering event at one location. The photon or light then travels in a different direction, w', along ray line 28. For other photons or light along the ray 26, the scattering may occur at other locations or not at all, depending on the probabilities. The direction of scattering even for the same location of interaction may be different. By combining the simulation from many photons or light samples, the value for the pixel is determined.

The photon or light interaction may be modeled based on any one or more probabilities. For example, the probability of absorption, probability of scattering, and/or probability of emission are modeled. In one embodiment, there are three forms of photon-volume interactions: absorption—light absorbed by the volume, emission—light emitted from the volume, and scattering—light direction changed by the volume. Each light photon could scatter to a random direction when the photon encounters the samples within the volume. According to a random probability, which is a function of the volume intensity, the photon may also be absorbed and thereby not contribute to the final image. The scattering probability and the new photon direction are computed with a function of the density of the encountered sample (e.g., the phase function). The following differential equation accounts for these interactions:

$$\frac{dI(x, \omega)}{ds} = -\sigma_t(x, \omega)I(x, \omega) + \qquad \text{(Eqn. 1)}$$

$$\sigma_e(x, \omega)I(x, \omega) + \sigma_s(x, \omega)\int_\Omega f(x, \omega, \omega')I(x, \omega')d\omega'$$

where x is the spatial location in the volume where interaction is being modeled, ω and ω' are the ray path direction for the ray from the pixel and after scattering, respectively, $\sigma_t(x, \omega)$ is the absorption probability function, $\sigma_e(x, \omega)$ is the emission probability function, $\sigma_s(x, \omega)$ is the scattering probability function, and f (x, ω, ω') is the phase function. Other representations may be used for modeling the interaction, such as using fewer probabilities. In an alternative embodiment, the probability of scattering is modeled in the Monte Carlo simulation without Monte Carlo simulation of emission and/or absorption.

The probability functions in the equation are a function of the three-dimensional sampling position. For each position that a photon or light intersects, the probability of interaction is calculated. As the photon travels along the ray path, including or not including scattering, the probabilities of interaction are determined.

The differential equation does not have any analytic solution in the case of rendering from medical data or other non-planar or spherical surfaces. Ray tracing with Monte Carlo integration is applied to get the numerical solution. Other approaches using random generation or other technique may be used. Photons are created from light sources toward the camera. In terms of gathering the photons at the pixel locations, light paths are created from the viewpoint, through pixels in the viewport and toward the light sources. The gathered light samples are then accumulated at the pixel locations to produce the image. In bi-directional path tracing for example, light paths originating at both the viewpoint and the light sources are considered. More advanced methods use these to generate nearby light paths directly. As the number of samples gathered increases, the average light intensities accumulated for photons or light samples converge to the numerical solution of the pixel color or intensity. In medical visualization, the probability functions may be simplified to be a one-dimensional function of the volume intensity at the sampling position.

Any number of samples may be provided. For a final or complete rendering, the number of samples may be greater than 500, such as 1,000 samples per pixel. The number may be set or user selected. Alternatively, the number is based on a set or user selected time—add samples until a threshold period.

Figures 3A, 3B:
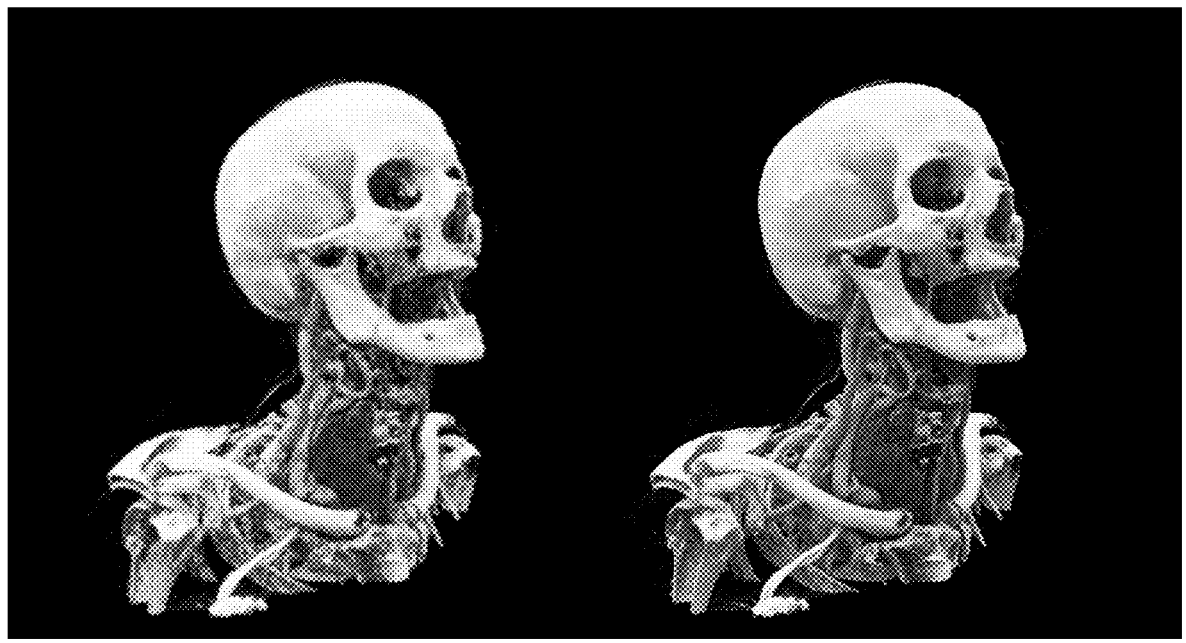
FIG. 3A is an example physically-based rendered image during interaction.
FIG. 3B is an example physically-based rendered image after 1000 samples per pixel.
Figures 4A, 4B, 4C:
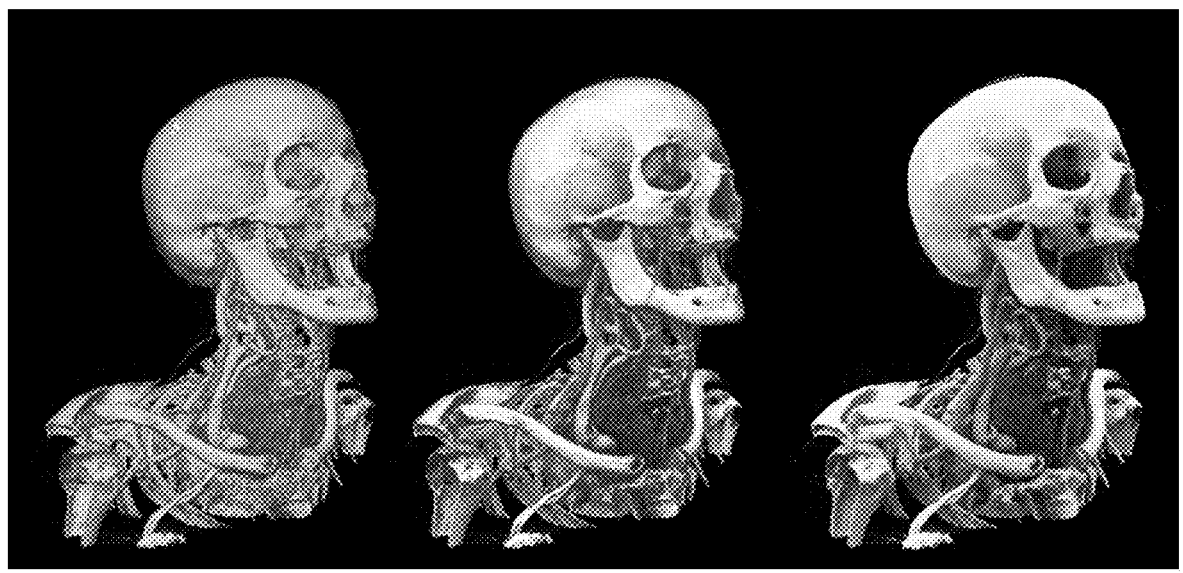
FIG. 4A is an example raycast rendered image.
FIG. 4B is an example raycast rendered image with ambient occlusion and color correction augmentation.
FIG. 4C is an example physically-based rendered image.

FIGS. 3B and 4C show the same image. The image is a physically-based rendering using Monte Carlo-based ray tracing modeling scattering and absorption without emission. 1,000 light samples per pixel are used.

If the viewer wants to change the rendering, then the user adjusts one or more settings of one or more rendering parameters. For example, the user views the image of FIG. 3B, but wants to see the right side of the patient so alters the 3D camera position. As another example, the user wants to see different soft tissue relative to the skeleton, so adjusts the transfer function classification or window function to reveal different parts. In another example, the user wants to clip part of the volume to view structure behind displayed tissue or bone, so the user adjusts a clipping plane or other clipping position. In yet another example, the user wants to use different lighting to highlight a different region, so the user adjusts lighting manipulation. Other adjustments may be provided.

In act 12 of FIG. 1, the user input device or user interface receives this interaction by the user. The user input or interface receives a user setting of a rendering variable. In an alternative to user input, a change in a setting is acquired from memory or provided from a source other than the user. Instead of user setting, a default, predetermined, or application-specific setting different than for the initial image is received.

Any change to one or more input parameters or user interaction triggers a switch to the interactive mode or phase. A check for interaction is performed. If a user input of a change to a setting for rendering is detected, then the change in the rendering parameter or parameters is made and the interaction mode of rendering and settings is entered.

A sequence of images is displayed. The initial image may be statically displayed or progressively displayed. For progressive display, the physically-based rendering is performed iteratively. As more light samples per pixel are calculated, the pixel values are updated. This progressively forms the image on the display until the threshold number of samples occurs or until interaction is triggered.

The sequence includes images rendered for interaction. Once interaction is triggered or occurs, other images of the same volume of the same patient are generated. During interaction, at least part of the rendered images is rendered with raycasting. This allows generation of images animating or gradually altering from a previous image to an image with an updated setting. For example, the user adjusts a camera position or transfer function (e.g., window), and an image is generated for each setting over the adjustment range. Images for settings between the user selected ones may be provided to transition between the settings. In another example, the user changes from one setting to another. The renderer generates a series of images gradually transitioning between the two settings. In other embodiments, the image with the new setting is generated without gradual transition.

The sequence includes a subsequent physically-based rendered image. Once the interaction ends, physically-based rendering is performed. The transition between direct volume rendering during interaction and physically-based rendering after interaction may be direct, replacing one type of rendering with the other. Alternatively, the images from both types are blended together.

Acts 15-18 show one example of rendering the sequence of images. In act 15, one or more (e.g., a sequence of images reflecting changes in rendering) two-dimensional (2D) images are rendered to a display during interaction by a user. Based on a currently or previously displayed image of the volume, the user changes a setting. A new image is rendered to the display from the intensities based on the change.

For this interactive rendering, direct volume rendering is used. Any direct volume rendering may be used, such as isosurface rendering, slab rendering, or raycasting. For raycasting, alpha blending, maximum intensity projection, or other rendering may be used. Rays are cast from a camera position through the volume to pixels on an image plane. The intensities or voxels along each ray are used, with a transfer function, to determine the color (e.g., RGB) value for the pixel. For medical image visualization, the interactive rendering is provided by a fast single-pass raycaster for 3D volume data. Other raycasting may be used, such as forming rays at sub-pixel positions to average for a given pixel to avoid artifacts.

For the images generated with raycasting during interaction, the images are generated at any rate. In one embodiment, the images are generated at least at 20 frames per second. In other embodiments, the images are generated at a real-time rate, such as 30 or more frames per second. 20 or more frames per second provides a user experience during interaction where the sequence of images does not appear jumpy or jittery, instead smoothing transitioning between images as one or more settings are changed. By rendering 20, 30, or more frames per second, an interactive or real-time frame rate is maintained during user interaction to change a physically-based volume rendering. Raycasting allows for this frame rate as physically-based volume rendering, where internal caching is not sufficient, renders images at a slower rate or provides incomplete images at this rate.

The rendering settings for the raycasting are set to provide a similar look and feel as the physically-based rendering. A look-up table based on a perception metric or based on user ranking may relate different combinations of settings for one type of rendering to combinations of settings for another type of rendering. A machine-learnt classifier may be used to determine the settings for one type of rendering based on settings for another type of rendering. Calibration or other matching may be used. The relationship is to maintain or preserve cohesive perceptual details despite the use of the two different types of rendering.

Other approaches may also be used in addition to or alternative to a look-up table or machine-learnt relationship. In one embodiment, during interaction, information from physically-based rendering is included in the images from the raycasting. For example, a small number of light samples are blended in by computing a very coarse low-resolution path traced image used to color-correct the raycast image (e.g., light paths with only 1 light bounce are computed to produce shadows or an ambient occlusion effect). The information is blended with the 2D images from raycasting. To further enhance the fidelity of the interactive to the final rendering, the renderer may blend a small number of samples from the final renderer (i.e., physically-based rendering) with the images from raycasting to show a preview of the final image effects during interaction.

To limit the processing burden, the information from the physically-based rendering is provided for only a sub-set (i.e., less than all) of the pixels of the 2D images. Any size sub-set may be used, such as less than ½, ⅓, or ¼ of the pixels.

The locations of the pixels of the sub-set are selected to be at locations of interest. In one embodiment, the center pixels are treated as the location of interest. In other embodiments, anatomy associated with the type of imaging or imaging application determines a region of interest.

In other embodiments, the pixels of the sub-set are selected based on a surface boundary, color similarity, and/or shading similarity. The most salient features that are desirable to be preserved are used to select the sub-set. A filter, segmentation, or other detector may be applied to find one or more anatomical structures, such as surface boundaries. The sub-set is the pixels representing the detected surface boundary. Any surface boundary approximation that closely matches allows for blending. In another example, the colors of pixels from raycasting are compared to the colors from the previous or initial physically-based rendering. Pixels with similar color (e.g., within a threshold color difference) form the sub-set. In yet another example, shading similarity is used. The key aspects of shading, such as specular highlighting or ambient diffusion, are measured in the raycasting image and the previous physically-based rendered image. Where the values are similar, the pixels are included in the sub-set. Where the sampling of both raycasting and path tracing implementations closely match, the blending occurs. Where there is less match, then raycasting is used without path tracing. The goal is to have similar rendering computed through the volume in both approaches.

The classification methods, such as preintegration tables and/or blending method for the rendering integral, are matched. Since the different types of rendering use different approaches for classification, the calibration or matching relates the types of rendering to each other. In one embodiment, the voxel classification method and the related rendering settings (e.g., ray step size during raycasting) are matched between the raycasting and the path tracing to ensure consistent visualization of structures in the data. In a different embodiment, the raycasting method may use a faster approximation for the classification (e.g., lower resolution pre-integrated look-up table with a larger step size) or the classification may be used to capture some of the path tracing lighting effects. In both cases, the classification and related settings during raycasting may be modified to more closely match the final path traced image. Possible approaches include machine learning or heuristic techniques for deriving a different look up table or different rendering parameters or deriving a higher-order classification function (e.g., 2D, curvature-based or shape-based).

For pixels where blending is not to occur, the pixel values determined by raycasting are used. For the sub-set of pixels, the pixel values from the raycasting are blended with the pixel values from path tracing. The pixel values from the path tracing may be from the initial or previously physically-based rendering, with or without temporal extrapolation or reprojection. Alternatively, the pixel values from the path tracing are rendered given the current settings. A fewer number of samples, such as 16 per pixel, and/or size of the sub-set are used to render with path tracing, allowing for interactive frame rates in physically-based rendering. Different optimization may be used, depending on the number of samples per pixel.

Any blending may be used, such as averaging. Weighted averaging may be used to control uniformity across the entire image relative to amount of information from path tracing to add. The amount of blending or weights may be programmable or set by the user. Alternatively, the weights may be set by a heuristic function, a machine learning approach or a different denoising operation.

In another approach to make the raycast images have perceptual coherence with the physically-based renderings, the rendering parameters of the direct volume rendering and/or the physically-based rendering adapt. During the interaction phase, the renderer may further adaptively modify one or more rendering parameters. The rendering with raycasting and/or the rendering with path tracing for the sub-set adapt. The setting for each of one or more rendering parameters is altered.

The adaptation is based on user interactions or a metric of the rendering (e.g., based on collected or computed metrics from the renderer itself). For example, the rendering resolution or image quality (e.g., contrast, artifact reduction processing, and/or step size for sampling along a ray) adaptively changes to maintain a constant or regular interaction frame rate. The size of the sub-set and/or number of samples for information from path tracing may be increased or decreased based on the frame rate. The raycasting may be changed based on the frame rate, such as altering when the frame rate drops below or goes above a threshold by a given amount. In another example, filtering parameters (e.g., spatial filtering) adapt based on a noise metric. The noise or signal-to-noise ratio for the intensities representing the volume and/or for the rendered image is calculated. The rendering adapts based on the noise level, such as to allow more noise or remove more noise. More filtering is applied for noise level above a threshold. In another example, the lighting or camera parameters for rendering adapt based on image metrics. Any lighting metric, such as brightness for a region of interest or over the entire image, is used to control settings of lighting. The brightness or other lighting characteristic is altered based on measured brightness or another characteristic.

To improve image quality, the rendering with raycasting or the blended combination of raycasting and path tracing uses adaptive filtering. The rendered image is filtered adaptively. Spatial or anti-aliasing filtering adapts during interaction. The filtering strength or kernel used is dependent on the rendering settings. For example, raycasting casts N rays for each pixel, slightly offset from each other. N varies based on the rendering settings. Settings that require more processing have a smaller value for N than settings the require less processing. In one embodiment, raycasting with N=4 samples (i.e., rays) per pixel uses less filtering than blending raycasting with a small number of path traced samples for a sub-set of pixels. Other mappings of rendering settings to filtering may be used.

In another embodiment to make the raycast images have perceptual coherence with the physically-based renderings, the raycast images are augmented. The 2D images rendered by direct volume rendering during interaction are altered to include one or more alternative visual representations. A graphic, glyph, or pixel value variation is added to the image.

The graphic, glyph, or variation is a visual representation of an expected image feature of the physically-based rendering. The augmentation is based on one or more settings for the path tracing. For example, the depth-of-field camera effect may be represented by a focal plane and a glyph for the focal distance in the raycast image. The lensing effect used in path tracing may be simulated on the raycast image. A graphic representing the focal plane and a marker (e.g., glyph) is added at the focal distance. In another example, clip planes for path tracing are rendered using laser lines, in-painting, plane outline, or other graphic representing the clip plane in the raycast images. In another example, lighting effects are stylized, such as using contour lines, cartoon shading, silhouette shading, and/or other augmentation.

In another embodiment, the renderer renders with settings of the direct volume rendering set based on image differences between the direct volume rendering and the path tracing rendering. Based on the previous or initial physically-based rendered image, the interaction provides a desired change. Thus, information about what the desired image looks like is available. For example, the previous image is too dark (e.g., average brightness for a region or entire image is at a level). The interaction is to increase the brightness. A desired brightness level is chosen. The renderer settings for the raycasting adapt to provide the desired brightness level. The adaptation minimizes the difference between the desired brightness level and the brightness level of the rendered image. Similarly, the rendering settings for the path tracing are set to minimize the difference from the brightness level, resulting in similar perceptual brightness of images during interaction and after interaction.

The image difference between the set level or between raycast images and path tracing images during transitions between interactive and final rendering are minimized or maximized. The path tracing used during interaction may adapt to minimize or maximize the difference with the desired path tracing image after interaction.

One example includes applying a global or locally-adaptive color correction. The 3D look-up table for raycasting (e.g., 3D LUT for color correction or color grading) is set to match or minimize a difference with the 3D look-up table for path tracing. In another example, lighting parameters or lighting modes for raycasting are set to provide similar lighting parameters or lighting modes as for path tracing, such as use of light probe verses artificial light or use of light position. In yet another example, the number of path tracing samples used during interaction is gradually changed. For the sub-set of pixels, the number of samples of light for each pixel changes to minimize a difference between the raycasting and path tracing.

The parameter changes based on data and/or user-based heuristics or by machine learning. For example, a convex object represented in the data is detected. The path tracing uses a larger step size and lower resolution for contribution to the images during interaction to speed up the interaction. In another example, a concave object is detected. The lighting for the path tracing contribution during interaction is changed.

In other embodiments, the raycasting performed during the interactive phase uses pre-computed data to improve the rendering performance during interaction or to ensure that the image shown during interaction more closely resembles the final image. Pre-computed data may be pre-computed shadows, ambient occlusions, irradiance, reprojection from previous image results (e.g., using point clouds, lightfields), preintegration data, empty space skipping, or other data used for rendering but which may be computed for the volume prior to rendering an image. This pre-computed data may be used in path tracing and/or in raycasting.

In one embodiment, ambient occlusion is pre-computed. The intensities as distributed in the voxels are used to determine occlusion. An occlusion map for ambient light is created. The map, for a given position in the volume, provides the amount of ambient light that reaches that location, accounting for nearby volume structures. For example, the shape of surfaces is detected, or the surrounding intensities are used in a localized lighting simulation. This pre-computed data is used to modulate the ambient term of the shading computation and approximates the light occlusion from nearby surfaces without explicit tracing of additional light paths. The color of pixels is corrected based on ambient occlusion. In alternative embodiments, the ambient occlusion is precomputed for a given view in screen-space, such as by tracing the depth buffer for a given iso-surface, or by tracing additional ambient occlusion rays for a representative sample (or multiple representative samples) along the viewing ray. The additional ambient occlusion rays originate from a position in the volume with randomized direction and are traced only a short distance to check for nearby occlusion.

In other embodiments, data from a previous rendering is used, such as data progressively updated in path tracing during interaction or from rendering prior to interaction. This previous data is used for blending with the raycasting. The data may be blended directly or reprojected based on camera movement information and approximate depth information. Various heuristics may be used to obtain representative depth for a viewing ray, such as the maximal voxel opacity along the ray or thresholding of the accumulated opacity. Multiple depth values per ray may be used as well.

The interaction ends in act 16. The interaction is based on receiving user adjustments to one or more settings. When a change is not received for a given period, the interaction phase is over. Any threshold period may be used, such as 1 or 2 seconds. In other embodiments, the type of rendering changes immediately upon not receiving an interaction or user input.

In one embodiment, the period adapts to a metric. An adaptive time-out is used. A heuristic approach is used. One example usage is with high-latency systems, such as where cloud-based resources (e.g., a server) perform the rendering. Immediate switching to path tracing upon ending of interaction may trigger rapid toggling where the user or network causes delay in receipt of further interaction. This may occur even under constant interaction. By setting the period or time-out based on a measure of network latency or time for interaction for a given or average user of the network, the time out adapts to avoid rapid toggling, improving the user experience.

The lack of interaction triggers ending of raycasting for rendering and the beginning of physically-based rendering. Alternatively, the physically-based rendering begins for pixels not in a sub-set and continues for pixels of the sub-set. Once interaction ends, progressive rendering of final image begins. Physically-based rendering is performed to render an image or series of images as the additional sampling per pixel is used to progressively update the image. The image is rendered by just path tracing. In other embodiments, the image is a blend from both raycasting and path tracing.

In one embodiment, the end of interaction triggers a transition in act 17. The raycasting used for rendering during interaction may simply be replaced by an image or images rendered by path tracing. For a transition, raycasting is blended with the physically-based rendering. This blend gradually transitions from the direct volume rendering used for interaction to the physically-based rendering used for diagnosis or treatment planning. The rendering transitions from the rendering of the sequence of images during interaction to the rendering of the 2D image with path tracing. The displayed images, however, transition by blending. During the transition, a blend of the 2D image currently being rendered with path tracing with at least one of the 2D images rendered with raycasting occurs.

The transition between interactive and final rendering preserves cohesive perceptual details. The blending adapts the perceptual understanding of the interactive to the final image content. The transition animates the switch from the interactive to the final imaging. The results are presented to the user in real-time or at an interactive rate.

The interaction ends once the viewer believes the settings are as desired. Thus, a last 2D image rendered with raycasting represents the volume with the desired settings, at least at that point in time. This direct volume rendered image is perceptually similar to the desired physically-based volume rendered image. Thus, this last raycast image is blended with the image or images from the physically-based rendering.

For physically-based rendering, the 2D image is assembled by stochastically sampling for each pixel many times. The image may be progressively rendered as samples are added, such that some or all the pixel values are updated as further sampling occurs. The completely rendered image with all samples may be used for blending. In one embodiment, the initial image in the progression is used for blending. In yet other embodiments, different images of the progression are used over time, such as blending the raycast image with a progression of path tracing images.

The transition occurs for a fixed time, such as a few seconds. Alternatively, the transition occurs for a given number of sampling updates of the progression. For example, the transition occurs until the last sampling update in the progression. As another example, the transition occurs over the initial N updates, such as the first 10 updates out of 100 in the progression.

Any blending may be used. An average combines the pixel values from the two types of rendering. Other functions than an average may be used. In one embodiment, a weighted average is used. The weights shift over time, so that, initially in the transition, the direct volume rendering is weighted more heavily and, later in the transition, the physically-based volume rendering is weighted more heavily.

In one embodiment, the blending adapts as a function of an image feature. The image features are detected in a raycast image and/or a path tracing image. In one embodiment, the feature is in one of the images to be used for blending, but other images generated prior to blending may be used. The weights or type of blending used is based on the image feature. Any image feature may be used, such as perceptual difference of objects in the images, measured image noise, or image resolution. For example, the contribution from direct volume rendering is weighted less where an edge is perceptually different in the direct volume rendering than in the physically-based rendering. As another example, the type of rendering contributing the most noise is weighted less, or the change in weighting over time emphasizes the types of rendering contributing less noise. In other embodiments, the weighting is based on the progression for the path tracing. More rapid progression or updating results in more quickly altering the weight to favor the physically-based rendering.

Where the user views the physically-based rendered image and decides to make further changes, the rendering transitions back to raycasting for the interaction. The animation may be different for the progressively rendered image to interactive transition, or no animation may be used at all. This transition may be direct, without blending, or may include blending to animate the transition. In one embodiment, re-projection from the physically-based rendered image is used for blending over a short time during a change in camera position as the interaction.

After the transition, the renderer renders using the physically-based rendering in act 18. Upon the interaction ceasing for a period and/or after the transition, a 2D image is rendered to a display from the intensities with physically-based rendering, such as with path tracing. This physically-based rendering progressively updates the 2D image with pixel values calculated from additional sampling in the path tracing. The 2D image is rendered iteratively using the physically-based path tracer. The path tracing computations are then performed progressively, looping until the renderer achieves the desired image quality (e.g., 1000 samples per pixel, or a fixed time interval). The pixels are all updated together, such as the pixel values calculated for each pixel using a given number of additional stochastic samples. Alternatively, some pixels are updated, and others are not. In yet other embodiments, the image is not rendered to the display until all the sampling is complete.

In one embodiment, Monte Carlo path tracing is used with per-pixel sampling. Cached data structures may be used and/or updated. Raycasting is not used, so the image is from physically-based rendering alone. Alternatively, direct volume rendering is blended with the physically-based rendering, but with fixed weighting and/or weights making a majority of the contribution form the physically-based rendering. The settings of the rendering parameters for physically-based rendering may be based, in part, on the interaction and/or on settings used during interaction. Calibration, matching, or other relationship is used to relate settings from the raycasting to settings for path tracing. Filtering, compression, or other operations may be performed and may be based on operations used in the rendering for direct volume rendering.

The rendered image is transmitted. The transmission is to a display, such as a display buffer. The output of the display buffer to the display generates the image for viewing. During progression, the display buffer is updated with new or different pixels values where further sampling results in a change. Once rendering is complete (e.g., all sampling performed), the static image remains on the display until any subsequent interaction. The rendered image or images are displayed by the renderer on the display. The image represents the patient. Alternatively, the image is transmitted to a network or memory, such as a picture archiving communications system.

The feedback from act 18 to act 12 represents returning to an interaction phase. The viewer may decide again to change the rendering, such as the camera position, window, transfer function, lighting, or other controllable characteristic of rendering. After any or no transition from physically-based rendering to direct volume rendering, the interaction phase provided by act 15 is begun.

FIGS. 3A and 3B illustrate physically-based rendering without using raycasting during interaction. FIG. 3A shows an image rendered during interaction (i.e., in an interactive mode). FIG. 3B shows an image rendered after completing 1000 samples per pixel. The interactive mode uses the same Monte Carlo path tracing technique and parameters as the final rendering. The sampling pattern during interaction is tuned to minimize the perceptual difference with the expected final image (e.g., the random number generator uses a fixed key identified to provide a similar image with fewer samples). Only 16 samples are used per pixel for interaction and at reduced image resolution (e.g., ½ resolution in each dimension), providing the image of FIG. 3A at interactive framerates (approx. 60 ms per image). While the overall impression matches well, the interactive rendering is slow and the resolution is not sufficient for critical evaluation of the data. The interaction is delayed, resulting in stuttering in imaging or requiring patience by the viewer. The image during interaction is noisy due to the small number of samples per pixel.

FIGS. 4A and 4B show example images rendered during interaction before rendering the physically-based image of FIG. 4C. FIG. 4C is the same image as FIG. 3B, rendered with Monte Carlo path tracing using 1000 samples per pixel.

FIG. 4A represents one configuration for interactive rendering. This configuration uses raycasting with alpha blending. The settings of the raycasting and path tracing parameters are matched to produce similar color and opacity perception. This interactive image does not show any global illumination effects (e.g., shadows, ambient occlusions, color bleeding). In the hybrid renderer during interaction, the shadowing effects are not visible during interaction and the perceptual image change from FIG. 4A to FIG. 4C is jarring, even if the transition from interactive to final image quality is smoothed with blending. Since raycasting is used, stuttering or jitter during interaction is minimized. The raycasting allows the user to more rapidly interact with the data (e.g., windowing, clipping, view changes), so more quickly end up with the final desired physically-based rendered image.

FIG. 4B represents another configuration for interactive rendering. This configuration uses raycasting with alpha blending. In addition to matching the data classification and the opacity handling, the direct volume rendered image is augmented. The augmentation is on-the-fly ambient occlusion computation and color correction. The occlusion computation is performed at the end of ray-casting. The color correction to emulate ambient occlusion is applied to the raycast image. The interactive image of this configuration more closely resembles the final image (i.e., FIG. 4B appears more similar to FIG. 4C than FIG. 4A is similar to FIG. 4C). Due to the ambient occlusion augmentation, a major component of the global illumination effect may be previewed during interaction and the 3D shape perception is enhanced during interaction.

In both cases (i.e., FIG. 4A and FIG. 4B), the image during interaction is sharper, noise-free or less noise, and at improved framerate compared to the non-hybrid approach (i.e., FIG. 3A).

FIG. 5 shows one embodiment of a system 50 for interactive rendering in medical imaging. The system 50 renders a volume of a patient for medical visualization. Ray tracing or other physically-based rendering is desired. For interaction, raycasting or other direct volume rendering is used to avoid the delays associated with physically-based rendering. Various settings, augmentations, adaptation, and/or blending may be used to maintain a similar appearance, at least for one or more perceptual characteristics, between the direct volume rendered images and the physically-based volume rendered image.

The system 50 includes a medical imaging system 52, a user input or interface 54, a renderer 56, a memory 58, and a display 60. Additional, different, or fewer components may be provided. For example, a network or network connection is provided, such as for networking with a medical imaging network or data archival system.

The user interface 54, renderer 56, memory 58, and display 60 are part of the medical imaging system 52. Alternatively, the user interface 54, renderer 56, memory 58, and/or display 60 are part of an archival and/or image processing system, such as associated with a medical records database workstation or server. In other embodiments, the user interface 54, renderer 56, memory 58, and/or display 60 are a separate computer, such as desktop or laptop, a workstation, a server, a network, or combinations thereof. The user interface 54, renderer 56, memory 58, and display 60 may be parts of different systems, such as the memory 58 being in a picture archiving and communications system (PACS), the renderer 56 being part of a workstation, and/or the display 60 being an imaging system or radiological display.

The system 50 is configured to implement the method of FIG. 1. Alternatively, other methods are implemented.

Any medical imaging system 52 may be used. For example, the medical imaging system 52 is a CT, MR, ultrasound, x-ray, fluoroscopy, angiography, or emission tomography (i.e., functional imaging such as PET or SPECT) system. The medical imaging system 52 is any now known or later developed medical imaging system for scanning an interior of the patient. The medical imaging system 52 is configured by hardware, firmware, and/or software to scan a patient.

The medical imaging system 52 is configured to scan an internal region of the patient. The surface or skin of the patient may or may not also be scanned. Any portion or extent of the patient may be scanned, such as a scan of an organ, torso, extremity, or full body. The scan acquires data representing the interior of the patient. The represented portion includes a volume or three-dimensional distribution of response from the patient. FIG. 2 shows an internal region 22 as a cube, but the scanned volume of the patient may have any shape.

The medical imaging system 52 is configured to scan the patient to acquire at least one set of data, generating voxel data representing a scanned volume of the internal region. The set or frame of data represents the internal region of the patient at a specific time or period. A static volume is acquired. Alternatively, the scanning is repeated or performed in an ongoing manner to acquire a sequence of sets of voxel data.

The scan data may be output as a 3D reconstruction or data representing a volume. Alternatively, the acquired scan data is reconstructed to represent the volume. For example, Fourier processing is applied to k-space data in MR to reconstruct the volume. As another example, computed tomography is used to reconstruct the volume (e.g., SPECT or CT). In yet another example, data representing three dimensions in a scan format is interpolated to a regular or other grid, such as a Cartesian coordinate grid. Each datum is associated with a different volume location (voxel) in the patient volume and assigned a scalar intensity.

The data from the scan is formatted as voxels in an isotropic grid. For example, voxels in a 512×512×512 Cartesian grid are used. Anisotropic grids may be used. Other formats may be used, such as the data representing locations in a polar coordinate format. For each voxel or location, a scan response is provided by a scalar value (e.g., 16-bit dynamic range), but other representations may be used, such as RGBa values.

Given the number of different types of medical imaging systems 52, different workflows, different clinical applications, and uses for diagnosis or treatment, there is a large variety in the voxel data and characteristics of the voxel data in medical imaging. Any one or more sets of voxel data representing intensity of return, density, attenuation, elasticity, motion, uptake, temperature, molecular spin response, other characteristics, or combinations thereof may be acquired by the medical imaging system 52.

The user interface 54 is an input device with or without an output. Any input may be used, such as keyboard, button, slider, knob, track pad, mouse, track pad, or other sensor. The output may be on the display 60, an LED, light, or other output.

The user interface 54 is configured to receive input from the user. The input may configure the rendering. The user inputs a value or values for any number of rendering parameters, such as view direction, type of lighting, visual effect, or transfer function. For example, the user may interactively change one or more values of a setting. In one embodiment, the user rotates or alters the view direction for rendering. In other embodiments, the user selects the imaging application (e.g., cardiac imaging), resulting in loading of default settings. In alternative embodiments, a processor or the renderer 56 uses default or determined values for one, more, or all the settings.

When a setting is changed due to interaction, the rendering is performed again using the new setting. By rapidly re-rendering, such as at real-time or interaction rates, the interaction may appear smoother or appealing to the user. Multiple renderings may be generated for a single change, such as rendering a gradual transition from the original value to the input value of the rendering parameter. The images prior to and after adjustment use the same un-adjusted parameter values for other parameters for rendering. For example, a change in viewing direction is performed, but the windowing, classification, and/or other rendering parameters are preserved (e.g., values the same). The values of these other parameters may change, such as to adapt to the change by the user.

The renderer 56 is a general processor, central processing unit, control processor, graphics processor, digital signal processor, three-dimensional rendering processor, image processor, application specific integrated circuit (ASIC), field programmable gate array (FPGA), digital circuit, analog circuit, combinations thereof, or other now known or later developed device for rendering an image from data. The renderer 56 is a single device or multiple devices operating in serial, parallel, or separately. The renderer 56 may be a main processor of a computer, such as a laptop or desktop computer, or may be a processor for handling some tasks in a larger system, such as in an imaging system 52. The renderer 56 is configured by hardware, firmware, and/or software.

In one embodiment, the renderer 56 is a graphics processing unit (GPU) or a graphics card with rendering code. A set of graphics cards may be used. A GPU is a massively parallel computation device. CUDA or OpenCL languages are used to program the GPU. In other embodiments, the x86-based Xeon Phi or custom FPGA/ASIC implementations are used. One side effect of the ray-tracing pipeline is that the computations are generally performed per pixel in screen space, allowing for efficient scaling with multiple computational devices. Multiple GPUs in a render node, GPU clusters, CPU/GPU hybrid systems, or other computational architectures may be used. Sample-based, tile-based, or frame-based distribution of the rendering may be used.

The renderer 56 is configured to physically render an image from the voxel data. Any physical rendering may be used, such as ray tracing and Monte Carlo solution. The physical rendering uses a physics model, such as for photon or another path tracing, to render. Rays are traced from each of a plurality of pixels for the image, and the interaction of the light with the volume is modeled stochastically. For example, probabilities are used to model interaction (e.g., scattering).

Where the rendering is to be changed, the renderer 56 is configured to operate or render in an interactive mode. Upon detection of entry of a change in one or more settings of rendering parameters, the renderer 56 changes the type of rendering. During interaction, the renderer 56 renders images with raycasting or other direct volume rendering using the changed rendering parameters. Physically-based rendering may continue for a sub-set of pixels. The renderer 56 may be configured to augment the direct volume rendered images, to blend with information from physically-based rendering for some pixels, and/or to use rendering techniques or settings to match perceptual aspects of the raycast rendered image with the path tracing rendered image.

The renderer 56 is configured to continue direct volume rendering as long as the interactive mode continues. After a threshold amount of time since a last user input or change to a setting, the renderer 56 is configured to switch out of the interactive mode.

The switch directly returns to physically-based rendering or includes a transition. For example, the renderer 56 is configured to transition the displayed images from a direct volume rendered image to a physically-based volume rendered image. The transition includes at least one image in a sequence that is a blend of images from both types of rendering, such as averaging or weighted averaging of the color values of the direct volume rendered image with the physically-based volume rendered image.

The renderer 56 is configured to render 2D images of the volume from the voxel data with physically-based rendering at times outside of the period of interaction. The physically-based rendered images may be used for blending during transition and/or are used without direct volume rendering for times other than interaction and/or transition. When user input to change one or more settings is not occurring, then physically-based volume rendering is used. A rendered image or progression of images as more stochastic sampling occurs are rendered to the display 60.

The renderer 56 generates a sequence of images representing the internal region of the patient. The images may include images from direct volume rendering during interaction, images from physically-based volume rendering when interaction does not occur, and both for transition. For example, one of the images of FIG. 4A or 4B is output during interaction and the image of FIG. 4C is output when no interaction occurs. The generated images are scalar values or display color values (e.g., RGB) for pixels of the images. The images are output by transfer or loading into a display buffer.

The display 60 is configured to display the images output by the renderer 56. The display 60 is a monitor, LCD, projector, plasma display, CRT, printer, or other now known or later developed devise for outputting visual information. The display 60 is configured by receiving images, graphics, or other information from the renderer 56, memory 58, or medical imaging system 52. The display 60 receives the images rendered from the volume scan. The images are output to the user. The image represents the internal region of the patient.

The memory 58 is a graphics processing memory, video random access memory, random access memory, system memory, cache memory, hard drive, optical media, magnetic media, flash drive, buffer, database, combinations thereof, or other now known or later developed memory device for storing data. The memory 58 is part of the medical imaging system 52, part of a computer associated with the renderer 56, part of a database, part of another system, or a standalone device.

The medical scan data, reconstructions, voxel data, frames, rendering, settings, pre-computed data (e.g., caches), and/or images are stored. Any data used for imaging or data in beginning, intermediate, or final stages of processing are stored for access by the renderer 56.

The memory 58 or other memory is a computer readable storage medium storing data representing instructions executable by the programmed renderer 56 for interactive rendering in medical imaging. The instructions for implementing the processes, methods, and/or techniques discussed herein are provided on computer-readable storage media or memories, such as a cache, buffer, RAM, removable media, hard drive, or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for interactive rendering in medical imaging, the method comprising:
   scanning a volume of a patient with a medical scanner, the scanning acquiring intensities representing the volume;
   receiving, by a user input device, a user setting of a rendering variable;
   rendering, during reception of the user setting of a rendering variable, a sequence of first two-dimensional images to a display from the intensities with direct volume rendering;
   transitioning to path tracing rendering when the receiving of the user setting ceases for a period; and rendering, upon the receiving ceasing for the period, a second two-dimensional image to a display from the intensities with path tracing rendering.

2. The method of claim 1 wherein rendering the second two-dimensional image comprises progressively updating with additional sampling of the path tracing rendering.

3. The method of claim 1 wherein transitioning further comprises transitioning from the rendering of the sequence to the rendering of the second two-dimensional image with a blend of the second two-dimensional image with at least one of the first two-dimensional images.

4. The method of claim 3 wherein transitioning comprising transitioning for a first number of sampling updates of the second two-dimensional image or for a fixed time.

5. The method of claim 3 wherein transitioning comprises adapting the blend as a function of an image feature of one of the first two-dimensional images or the second two-dimensional image.

6. The method of claim 1 wherein rendering the sequence comprises rendering the first two-dimensional images at 30 or more frames per second in real time with the interaction by the user.

7. The method of claim 1 wherein rendering the sequence comprises rendering the sequence of the first two-dimensional images blended with data from the path tracing rendering for only a sub-set of pixels for the first two-dimensional images.

8. The method of claim 7 further comprising selecting the sub-set based on a surface boundary, color similarity, and/or shading similarity.

9. The method of claim 7 further comprising adapting rendering parameters of the direct volume rendering or the path tracking rendering as a function of the interaction and/or a metric of the rendering.

10. The method of claim 1 wherein the period adapts to a metric.

11. The method of claim 1 wherein rendering the sequence comprises rendering with adaptive filtering.

12. The method of claim 1 wherein rendering the sequence comprises augmenting the first two-dimensional images based on settings for the path tracing rendering.

13. The method of claim 1 wherein rendering the sequence comprises rendering with settings of the direct volume rendering set based on image differences between the direct volume rendering and the path tracing rendering.

14. The method of claim 1 further comprising:
receiving the interaction by the user as a change in a transfer function, camera position, clipping position, and/or light manipulation relative to a previous two-dimensional image rendered with the path tracing rendering;
wherein rendering the sequence comprises rendering after rendering and display of the previous two-dimensional image; and
wherein rendering the second two-dimensional image comprises rendering after the period occurs without the interaction.

15. A system for interactive rendering in medical imaging, the system comprising:
a medical imaging system configured to scan an internal region of a patient and generate voxel data representing a volume comprising the internal region;
a user interface configured to receive user input of one or more changes to rendering parameters;
a renderer configured to render first images of the volume from the voxel data with raycasting using the rendering parameters, the renderer configured to render the first images with the raycasting during a period within a threshold time of the receipt of any of the one or more changes, the render configured to transition to physically-based rendering at times outside of the period, and the renderer configured to render second images of the volume from the voxel data with physically-based rendering at times outside of the period, the times outside of the period being where user input of the one or more changes does not occur;
a display configured to display the first images and the second images as a sequence, the first and second images representing the internal region.

16. The system of claim 15 wherein the renderer is configured to transition from the first images to the second images with third images, the third images blending one of the first images with successive ones of the second images.

17. The system of claim 16 wherein the renderer is configured to output the first, second, and third images in real-time.

18. The system of claim 15 wherein the renderer is configured to render the first images as a blend of the raycasting with physically-based rendering for only a sub-set of pixels.

19. A method for interactive rendering in medical imaging, the method comprising:
physically-based volume rendering an internal region of a patient;
receiving a user interaction setting a rendering variable;
transitioning from physically-based volume rendering to raycasting based on the receiving of the user interaction;
maintaining a real-time frame rate during the receiving of the user interaction to change the physically-based volume rendering with raycasting; and
displaying a sequence of images including images from the physically-based volume rendering and the raycasting.

20. The method of claim 19 wherein displaying comprises displaying first images of the images from a blending of second images of the images from the physically-based volume rendering with a third image of the images from the raycasting.

* * * * *